US012285506B2

(12) United States Patent
Cambos et al.

(10) Patent No.: US 12,285,506 B2
(45) Date of Patent: *Apr. 29, 2025

(54) METHOD FOR IMPROVING THE SENSORIAL PROPERTIES OF OIL-IN-WATER EMULSIONS, TO REDUCE THE ADHESIVE EFFECT OF SUCH GLYCERIN-BASED OIL-IN-WATER EMULSIONS

(71) Applicants: SOCIETE D'EXPLOITATION DE PRODUITS POUR LES INDUSTRIES CHIMIQUES SEPPIC, Paris (FR); TOTAL MARKETING SERVICES, Puteaux (FR)

(72) Inventors: Sophie Cambos, Castres (FR); Emmanuelle Merat, Lautrec (FR); Cécile Taillebois, Salies (FR); Benjamin Swoboda, Orgeval (FR)

(73) Assignees: Societe d'Exploitation de Produits pour les Industries Chimiques SEPPIC, Paris (FR); TotalEnergies OneTech, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,030

(22) Filed: Dec. 1, 2023

(65) Prior Publication Data

US 2024/0099945 A1 Mar. 28, 2024

Related U.S. Application Data

(62) Division of application No. 16/470,350, filed as application No. PCT/FR2017/053507 on Dec. 12, 2017.

(30) Foreign Application Priority Data

Dec. 16, 2016 (FR) ..................................... 1662647

(51) Int. Cl.
| | | |
|---|---|---|
| A61K 31/4709 | (2006.01) |
| A61K 8/06 | (2006.01) |
| A61K 8/31 | (2006.01) |
| A61K 8/34 | (2006.01) |
| A61K 9/06 | (2006.01) |
| A61K 47/10 | (2017.01) |
| A61K 47/12 | (2006.01) |
| A61P 17/00 | (2006.01) |
| A61P 17/04 | (2006.01) |
| A61P 17/10 | (2006.01) |
| A61P 31/04 | (2006.01) |
| A61Q 19/00 | (2006.01) |
| A61Q 19/10 | (2006.01) |

(52) U.S. Cl.
CPC ................ A61K 8/062 (2013.01); A61K 8/31 (2013.01); A61K 8/345 (2013.01); A61Q 19/00 (2013.01); A61Q 19/10 (2013.01)

(58) Field of Classification Search
CPC . A61K 8/062; A61K 8/29; A61K 8/31; A61K 8/35; A61K 8/415; A61K 8/4946; A61K 8/4966; A61Q 17/04
See application file for complete search history.

(56) References Cited

U.S. PATENT DOCUMENTS

| | | |
|---|---|---|
| 5,004,598 A | 4/1991 | Lochhead et al. |
| 5,688,514 A | 11/1997 | Chaudhry et al. |
| 5,804,202 A | 9/1998 | Chaudhry et al. |
| 5,928,656 A | 7/1999 | Chaudhry et al. |
| 6,051,245 A | 4/2000 | Chaudhry et al. |
| 6,136,305 A | 10/2000 | Michel-lecocu et al. |
| 6,197,287 B1 | 3/2001 | Mallo et al. |
| 6,326,033 B1 | 12/2001 | Darmenton et al. |
| 6,346,239 B1 | 2/2002 | Mallo et al. |
| 9,226,889 B2 | 1/2016 | Braun et al. |
| 9,309,342 B2 | 4/2016 | Braun et al. |
| 2005/0175572 A1 | 8/2005 | Nguyen-Kim et al. |
| 2006/0167117 A1 | 7/2006 | Leaym et al. |
| 2008/0161418 A1 | 7/2008 | Dierker |
| 2010/0135918 A1 | 6/2010 | Kim et al. |
| 2013/0150322 A1 | 6/2013 | Paufique |
| 2015/0125403 A1 | 5/2015 | Joerger et al. |

FOREIGN PATENT DOCUMENTS

| | | |
|---|---|---|
| DE | 102015204662 A1 | 9/2016 |
| EP | 0503853 A2 | 9/1992 |
| EP | 0971683 A1 | 1/2000 |
| EP | 1889596 A1 | 2/2008 |

(Continued)

OTHER PUBLICATIONS

Agrana/Aak Sweden Ab, "Winter Comfort ECO / Conscious Hand Cream Maisita 9040," [Online], www.AGRANA.com, Oct. 24, 2016, 1 page.

(Continued)

Primary Examiner — Layla Soroush
(74) Attorney, Agent, or Firm — NIXON & VANDERHYE

(57) ABSTRACT

Disclosed is a method for improving the sensorial properties of an oil-in-water type emulsion for topical application, including, for 100% of its mass, 1% to 30% by weight of glycerol, characterised in that the oil-in-water type emulsion for topical application includes an effective quantity of a mixture of saturated cyclic or acyclic, linear or branched hydrocarbons, of which at least 95% by weight have between fifteen and nineteen carbon atoms. Also disclosed is a new oil-in-water type emulsion for topical use, including the mixture, and to the use of same in cosmetics.

4 Claims, No Drawings

(56) References Cited

FOREIGN PATENT DOCUMENTS

| FR | 2761595 A1 | 10/1998 |
|---|---|---|
| JP | 2007145719 A | 6/2007 |
| JP | 2012214448 A | 11/2012 |
| WO | 9844902 A1 | 10/1998 |
| WO | 2013128095 A1 | 9/2013 |
| WO | 2013132169 A1 | 9/2013 |
| WO | 2016146360 A1 | 9/2016 |

OTHER PUBLICATIONS

Anonymous, "Atomizing sprays for sun care applications," ip.com Journal, ip.com Inc., West Henrietta, NY, US, Nov. 30, 2006, XP013116940, 59 pages.
Anonymous, "Smooth Milk Body Lotion," Database GNPD [Online] Mintel, Nov. 2016, XP002772790, retrieved from http://www.gnpd.com, Database accession No. 4392919, 5 pages.
International Search Report, dated Mar. 2, 2018, from corresponding PCT application No. PCT/FR2017/053507.
Office Action issued in Korean Patent Application No. 10-2019-7019268 dated Dec. 20, 2022.

METHOD FOR IMPROVING THE SENSORIAL PROPERTIES OF OIL-IN-WATER EMULSIONS, TO REDUCE THE ADHESIVE EFFECT OF SUCH GLYCERIN-BASED OIL-IN-WATER EMULSIONS

CROSS-REFERENCE TO RELATED APPLICATIONS

This application is a divisional of U.S. application Ser. No. 16/470,350 filed Jun. 17, 2019, which was the U.S. national phase of International Application No. PCT/FR2017/053507 filed Dec. 12, 2017, which designated the U.S. and claims priority to FR 1662647 filed Dec. 16, 2016, the entire contents of each of which are hereby incorporated by reference.

BACKGROUND OF THE INVENTION

Field of the Invention

A subject of the invention is a novel method for improving the sensory properties of oil-in-water emulsions comprising glycerol and reducing their tacky effect.

Description of the Related Art

It is well known to thicken aqueous phases intended for cosmetic, dermopharmaceutical or pharmaceutical applications, in order to prepare oil-in-water type emulsions, by introducing synthetic or natural hydrophilic polymers therein. Natural polymers such as xanthan or guar gums are relatively widely used, but have the usual drawbacks of natural products (fluctuating price and quality).

This is why synthetic thickening polymers are widely used in the cosmetics or pharmaceutical industries. Thickeners that work over a wide pH range and have the advantage of being particularly well tolerated have already been proposed by several companies, including the applicant. Mention may especially be made of the synthetic thickeners described in U.S. Pat. Nos. 6,197,287, 6,136,305, 6,346,239 or else EP 0 503,853, or else U.S. Pat. No. 5,004,598. These polymers are in the form of an inverse latex or powder. They are essentially intended to thicken aqueous phases containing the different conventional constituents that can be found in topical formulations from the cosmetics or pharmaceutical industry. Mention will especially be made of oils, surfactants (nonionic or anionic), also referred to as emulsifiers, mineral salts and weak acids.

Some formulations, more particularly those intended for caring for the skin, also contain relatively large amounts of glycerol, typically between 5% and 10% by weight, in order to increase their moisturizing potential. However, since the presence of glycerol in these formulations also considerably increases the tacky effect thereof, producers add silicone oils thereto in order to limit or dispense with this tacky effect.

However, the addition of silicone oils makes the preparation of these formulas more complex. Moreover, the presence of silicone oils in formulas which are intended to be in direct contact with the skin is not well perceived by the final consumer. The cosmetics industry is therefore trying to limit the use thereof, and the applicant has in particular developed novel synthetic thickening polymers which were disclosed in the international applications published under the numbers WO2013132169 A1 and WO2013128095 A1, respectively.

However, these polymeric structures still involve the use of monomers bearing either silicone functional groups or fluoro functional groups, which the cosmetics industry is desirous to no longer use for environmental and regulatory reasons.

SUMMARY OF THE INVENTION

The inventors therefore sought to develop a novel solution to improve the sensory properties of a formulation, with the aim of reducing or dispensing with the tacky effect induced by the presence of glycerol, without it being necessary to thicken the aqueous phase with synthetic polymers comprising silicone or fluoro units or to add a third compound of silicone nature.

This is why, according to a first aspect, a subject of the invention is a method for improving the sensory properties of an oil-in-water type emulsion for topical use ($E_O$) comprising, for 100% of its weight, from 1% to 40% by weight of glycerol, more particularly from 5% to 30%, and even more particularly from 5% to 25% by weight of glycerol, characterized in that an effective amount of a mixture ($M_1$) of cyclic or acyclic, linear or branched saturated hydrocarbons, among which at least 95% by weight comprise from fifteen to nineteen carbon atoms, is incorporated into said oil-in-water type emulsion for topical use ($E_O$).

The term "effective amount" denotes, in the definition of the method as defined above, an amount such that the oil-in-water type emulsion for topical use (E) resulting from said method above:

exhibits a mean value of three measurements of the adhesion strength of less than or equal to 9 N, and more particularly less than or equal to 3 N, said adhesion strength being recorded during each of the measurements using a DHR2 rheometer (TA Instrument) equipped with a support of Peltier plate type, the temperature of which is set at 40° C., on which a plexiglass surface is placed, on which the emulsion to be tested is deposited, and exhibits a homogeneous appearance after storage for a duration of one month at a temperature of 45° C.

For the purposes of the present invention, the term "oil-in-water type emulsion for topical use ($E_O$)" denotes the emulsions comprising, for 100% by weight:

from 95% to 50%, more particularly from 90% to 70% of a cosmetically acceptable aqueous phase ($A_O$);

from 5% to 50%, more particularly from 10% to 30% of a fatty phase ($G_O$), said fatty phase ($G_O$) comprising, for 100% of its weight, from 1% to 12%, more particularly from 2% to 8% of at least one oil-in-water type surfactant and from 88% to 99%, more particularly from 92% to 98% of at least one oil and/or one wax.

For the purposes of the present invention, the term "oil" present in the fatty phase ($G_O$) of the oil-in-water type emulsion for topical use ($E_O$) as defined above denotes chemical substances or mixtures of chemical substances that are water-insoluble and that are in liquid form at a temperature of 25° C.

For the purposes of the present invention, the term "wax" present in the fatty phase ($G_O$) of the oil-in-water type emulsion for topical use ($E_O$) as defined above denotes chemical substances or mixtures of chemical substances that are water-insoluble and that are in solid form at a temperature of 45° C.

For the purposes of the present invention, the term "oil-in-water type surfactant" present in the fatty phase ($G_O$) of the oil-in-water type emulsion for topical use ($E_O$) as defined above denotes the chemical substance or the mixture of chemical substances that makes it possible to stabilize the droplets of said fatty phase ($G_O$) in dispersion in the continuous phase ($A_O$).

The following are examples of oil-in-water type surfactant present in the fatty phase ($G_O$) of the oil-in-water type emulsion for topical use ($E_O$) as defined above:

polysorbates resulting from the ethoxylation reaction between one molar equivalent of sorbitan esters and between 5 and 20 molar equivalents of ethylene oxide, and more particularly between one molar equivalent of sorbitan laurate, or of sorbitan palmitate, or of sorbitan stearate, or of sorbitan isostearate, or of sorbitan oleate, and between 5 and 20 molar equivalents of ethylene oxide;

the products resulting from the ethoxylation reaction between one molar equivalent of a fatty acid, for instance palmitic acid, myristic acid, lauric acid, stearic acid, isostearic acid, oleic acid, and between 5 and 40 molar equivalents of ethylene oxide;

the products resulting from the esterification reaction between a fatty acid, for instance palmitic acid, myristic acid, lauric acid, stearic acid, isostearic acid, oleic acid, arachidic acid, behenic acid, and between 4 and 20 molar equivalents, more particularly between 3 and 10 molar equivalents, of glycerol.

The expression "cosmetically acceptable" used in the definition of the aqueous phase ($A_O$) of the oil-in-water type emulsion for topical use means, according to the Council of the European Economic Community Directive no. 76/768/EEC of Jul. 27, 1976, amended by Directive no. 93/35/EEC of Jun. 14, 1993, any substance or preparation intended to be brought into contact with the various parts of the human body (epidermis, body hair and head hair system, nails, lips and genitals) or with the teeth and mucous membranes of the mouth, for the purpose, exclusively and mainly, of cleansing them, fragrancing them, modifying the appearance thereof and/or correcting body odors thereof and/or protecting them or keeping them in good condition. A cosmetically acceptable medium of these compositions which are a subject of the invention may conventionally contain water, one or more cosmetically acceptable organic solvents, or a mixture of water and one or more organic solvents. The cosmetically acceptable solvents may more particularly be chosen from polyhydric alcohols, for instance glycerol, diglycerol, glycerol oligomers, ethylene glycol, propylene glycol, hexylene glycol, diethylene glycol, xylitol, erythritol, sorbitol, or water-soluble alcohols.

According to one particular mode of the method as defined above, the term "effective amount of said mixture ($M_1$)" denotes a weight proportion of from 1% to 25% of the oil-in-water emulsion, most particularly from 5% to 20%.

The expression "for topical use" used in the definition of the method as defined above means that said composition is used by application to the skin, the hair, the scalp or the mucous membranes, whether it is a direct application in the case of a cosmetic, dermocosmetic, dermopharmaceutical or pharmaceutical composition or an indirect application, for example in the case of a body hygiene product in the form of a textile or paper wipe, or sanitary products intended to be in contact with the skin or the mucous membranes.

For the purposes of the present invention, the term "linear alkanes" present in the mixture ($M_1$) used in the method which is a subject of the present invention, and comprising from fifteen to nineteen carbon atoms, denotes more particularly the elements chosen from the group consisting of pentadecane, hexadecane, heptadecane, octadecane and nonadecane.

For the purposes of the present invention, the term "branched alkanes" present in the mixture ($M_1$) used in the method which is a subject of the present invention, and comprising from fifteen to nineteen carbon atoms, denotes more particularly the elements chosen from the group consisting of 2-methyltetradecane (or isopentadecane), 2-methylpentadecane (or isohexadecane), 2-methylhexadecane (or isoheptadecane), 2-methylheptadecane (or isooctadecane) and 2-methyloctadecane (or isononadecane).

For the purposes of the present invention, the term "cycloalkanes" present in the mixture ($M_1$) used in the method which is a subject of the present invention, and comprising from 15 to 19 carbon atoms, denotes more particularly saturated hydrocarbons comprising at least one saturated cyclic hydrocarbon-based group optionally substituted with one or more linear or branched alkyl radicals.

According to one particular aspect, a subject of the invention is a method as defined above, characterized in that said mixture ($M_1$) comprises, for 100% of its weight:

a weight proportion of branched alkanes of greater than or equal to 80% and less than or equal to 100%, and more particularly greater than or equal to 90% by weight, a weight proportion of linear alkanes of greater than or equal to 0% and less than or equal to 15%, and more particularly less than or equal to 10% by weight, a weight proportion of cycloalkanes of greater than or equal to 0% and less than or equal to 5%, and more particularly less than or equal to 1% by weight, and in that from 95% by weight to 100% by weight of said cyclic or acyclic, linear or branched hydrocarbons comprise from fifteen to nineteen carbon atoms and in that up to 5% by weight of said cyclic, acyclic, linear or branched hydrocarbons comprise less than fifteen carbon atoms or more than nineteen carbon atoms.

According to a more particular aspect, the subject of the invention is a method as defined above, wherein the mixture ($M_1$) is a mixture of saturated hydrocarbons sold under the brand name Emogreen™L15, comprising, for 100% of its weight:

i) 3.7% of linear alkanes comprising from fifteen to nineteen carbon atoms, ii) 96% of isoalkanes comprising from fifteen to nineteen carbon atoms, and iii) 0.3% of cycloalkanes comprising from fifteen to nineteen carbon atoms.

According to another more particular aspect, a subject of the invention is a method as defined above, characterized in that said mixture ($M_1$) comprises, for 100% of its weight:

a weight proportion of branched alkanes of greater than or equal to 40% and less than or equal to 100%, and more particularly greater than or equal to 50% by weight, a weight proportion of linear alkanes of greater than or equal to 0% and less than or equal to 20%, and more particularly less than or equal to 15% by weight, a weight proportion of cycloalkanes of greater than or equal to 0% and less than or equal to 40%, and more particularly less than or equal to 35% by weight, and in that 100% by weight of said cyclic or acyclic, linear or branched hydrocarbons comprise from fifteen to nineteen carbon atoms.

According to a most particular aspect, the subject of the invention is a method as defined above, wherein the mixture ($M_1$) is a mixture of saturated hydrocarbons sold under the brand name Emosmart™L19, comprising, for 100% of its weight:
  i) 13.20% by weight of linear alkanes comprising from 15 to 19 carbon atoms,
  ii) 55.00% by weight of isoalkanes comprising from 15 to 19 carbon atoms, and
  iii) 31.80% of cycloalkanes comprising from 15 to 19 carbon atoms.

According to another particular aspect of the method as defined above, the effective amount of said mixture ($M_1$) is such that the weight ratio between the glycerol and said mixture ($M_1$) is less than or equal to 10 and greater than or equal to 1, and more particularly less than or equal to 5 and greater than or equal to 2.

A subject of the invention is also an oil-in-water type emulsion for topical use (E) comprising, for 100% of its weight:
  from 40% to 90% by weight, more particularly from 60% to 90% by weight, and even more particularly from 70% to 90% by weight of a cosmetically acceptable aqueous phase (A) comprising, for 100% of its weight, from 5% to 30%, and even more particularly from 5% to 25% by weight of glycerol, and
  from 10% to 60%, more particularly from 10% to 40%, and even more particularly from 10% to 30% by weight of a fatty phase (G) comprising, for 100% of its weight, from 1% to 25% by weight, most particularly from 5% to 20%, of said mixture ($M_1$) of cyclic or acyclic, linear or branched saturated hydrocarbons, among which at least 95% by weight comprise from fifteen to nineteen carbon atoms, and from 0.5% to 15% of at least one oil-in-water type surfactant.

For the purposes of the present invention, the term "fatty phase (G)" denotes a fatty substance or a mixture of fatty substances that is insoluble in water and/or in mixtures of water and polar solvents. Such a "fatty phase" may comprise oils and/or waxes. Among the constituent elements of the fatty phase, mention may be made of:
  oils of animal origin, such as squalene or squalane;
  plant oils, such as phytosqualane, sweet almond oil, coconut oil, castor oil, jojoba oil, olive oil, rapeseed oil, groundnut oil, sunflower oil, wheat germ oil, corn germ oil, soybean oil, cottonseed oil, alfalfa oil, poppy oil, pumpkin oil, evening primrose oil, millet oil, barley oil, rye oil, safflower oil, candlenut oil, passionflower oil, hazelnut oil, palm oil, shea butter, apricot kernel oil, beauty leaf oil, sysymbrium oil, avocado oil, calendula oil, sesame oil, meadowsweet oil, macadamia/kiwi oil, borage oil, blackcurrant seed oil, coffee oil, pistachio oil, peach kernel oil, raspberry seed oil, strawberry seed oil, melon oil, blueberry seed oil, argan oil, oily plum extract, pomegranate oil, papaya oil, coconut milk oil, and oils derived from flowers or from vegetables;
  ethoxylated vegetable oils;
  synthetic oils, for instance fatty acid esters such as butyl myristate, propyl myristate, cetyl myristate, isopropyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate, isocetyl lanolate, fatty acid monoglycerides, diglycerides and triglycerides, such as glyceryl triheptanoate, alkyl benzoates, hydrogenated oils, poly(alpha-olefins), polyolefins such as polyisobutene, hydrogenated polydecene or hydrogenated polyisobutene, sold in France by Ets B. Rossow et Cie under the name Parleam—Polysynlane™, cited in: Michel and Irene Ash; Thesaurus of Chemical Products, Chemical Publishing Co, Inc. 1986 Volume I, page 211 (ISBN 0 7131 3603 0);
  silicone oils such as dimethylpolysiloxanes, methylphenylpolysiloxanes, amine-modified silicones, fatty acid-modified silicones, alcohol-modified silicones, silicones modified with alcohols and fatty acids, silicones modified with polyether groups, epoxy-modified silicones, silicones modified with fluoro groups, cyclic silicones and silicones modified with alkyl groups.
  waxes such as beeswax, carnauba wax, candelilla wax, ouricoury wax, Japan wax, cork fiber wax, sugar cane wax, jojoba wax, blackcurrant flower wax, narcissus flower wax, orange flower wax, orange wax, rice wax, paraffin waxes, lignite waxes, microcrystalline waxes, lanolin wax; ozokerite; polyethylene wax; silicone waxes; plant waxes; fatty alcohols and fatty acids that are solid at ambient temperature; glycerides that are solid at ambient temperature.

The term "oil-in-water type surfactant" present in the fatty phase (G) of the oil-in-water type emulsion for topical use (E) as defined above denotes a chemical substance or the mixture of chemical substances that makes it possible to stabilize the droplets of the fatty phase (G) in dispersion in the continuous phase (A). Mention may for example be made of:
  polysorbates resulting from the ethoxylation reaction between one molar equivalent of sorbitan esters and between 5 and 20 molar equivalents of ethylene oxide, and more particularly between one molar equivalent of sorbitan laurate, or of sorbitan palmitate, or of sorbitan stearate, or of sorbitan isostearate, or of sorbitan oleate, and between 5 and 20 molar equivalents of ethylene oxide;
  the products resulting from the ethoxylation reaction between one molar equivalent of a fatty acid, for instance palmitic acid, myristic acid, lauric acid, stearic acid, isostearic acid, oleic acid, and between 5 and 40 molar equivalents of ethylene oxide;
  the products resulting from the esterification reaction between a fatty acid, for instance palmitic acid, myristic acid, lauric acid, stearic acid, isostearic acid, oleic acid, arachidic acid, behenic acid, and between 4 and 20 molar equivalents, more particularly between 3 and 10 molar equivalents, of glycerol.

A cosmetically acceptable aqueous phase (A) included in the oil-in-water emulsion (E) as defined above may conventionally contain one or more cosmetically acceptable organic solvents, or a mixture of water and one or more cosmetically acceptable organic solvents. The cosmetically acceptable solvents may more particularly be chosen from polyhydric alcohols, for instance glycerol, diglycerol, triglycerol, glycerol oligomers, xylitol, erythritol, sorbitol, 2-methyl-1,3-propanediol; alkoxylated polyhydric alcohols; glycols, for instance butylene glycol, hexylene glycol, caprylyl glycol or 1,2-octanediol, pentylene glycol or 1,2-pentanediol, monopropylene glycol, dipropylene glycol, isoprene glycol, butyldiglycol, polyethylene glycols, the molecular weight of which is between 200 g·mol$^{-1}$ and 8000 g·mol$^{-1}$; or water-soluble alcohols, for instance ethanol, isopropanol or butanol.

The expression "cosmetically acceptable" used in the definition of the aqueous phase of the oil-in-water emulsion which is a subject of the present invention means, according to the Council of the European Economic Community Directive no. 76/768/EEC of Jul. 27, 1976, amended by Directive no. 93/35/EEC of Jun. 14, 1993, that said aqueous phase comprises water and any substance or preparation intended to be brought into contact with the various parts of the human body (epidermis, body hair and head hair system, nails, lips and genitals) or with the teeth and mucous membranes of the mouth, for the purpose, exclusively and mainly, of cleansing them, fragrancing them, modifying the appearance thereof and/or correcting body odors thereof and/or protecting them or keeping them in good condition.

According to one particular aspect, a subject of the invention is an oil-in-water emulsion (E) as defined above, characterized in that said mixture ($M_1$) comprises, for 100% of its weight:
- a weight proportion of branched alkanes of greater than or equal to 80% and less than or equal to 100%, and more particularly greater than or equal to 90% by weight,
- a weight proportion of linear alkanes of greater than or equal to 0% and less than or equal to 15%, and more particularly less than or equal to 10% by weight,
- a weight proportion of cycloalkanes of greater than or equal to 0% and less than or equal to 5%, and more particularly less than or equal to 1% by weight, in that from 95% by weight to 100% by weight of said cyclic or acyclic, linear or branched hydrocarbons comprise from fifteen to nineteen carbon atoms and in that up to 5% by weight of said cyclic, acyclic, linear or branched hydrocarbons comprise less than fifteen carbon atoms or more than nineteen carbon atoms.

According to this particular aspect, said mixture ($M_1$) is more particularly a mixture of saturated hydrocarbons sold under the brand name Emogreen™L15, comprising, for 100% of its weight:
i) 3.7% of linear alkanes comprising from fifteen to nineteen carbon atoms,
ii) 96% of isoalkanes comprising from fifteen to nineteen carbon atoms, and
iii) 0.3% of cycloalkanes comprising from fifteen to nineteen carbon atoms.

According to another more particular aspect, the oil-in-water type emulsion for topical use (E) as defined above is characterized in that said mixture ($M_1$) comprises, for 100% of its weight:
- a weight proportion of branched alkanes of greater than or equal to 40% and less than or equal to 100%, and more particularly greater than or equal to 50% by weight,
- a weight proportion of linear alkanes of greater than or equal to 0% and less than or equal to 20%, and more particularly less than or equal to 15% by weight,
- a weight proportion of cycloalkanes of greater than or equal to 0% and less than or equal to 40%, and more particularly less than or equal to 35% by weight, and in that 100% by weight of said cyclic or acyclic, linear or branched hydrocarbons comprise from fifteen to nineteen carbon atoms.

According to this particular aspect, the mixture ($M_1$) is more particularly a mixture of saturated hydrocarbons sold under the brand name Emosmart™L19, comprising, for 100% of its weight:
i) 13.20% by weight of linear alkanes comprising from 15 to 19 carbon atoms,
ii) 55.00% by weight of isoalkanes comprising from 15 to 19 carbon atoms, and
iii) 31.80% by weight of cycloalkanes comprising from 15 to 19 carbon atoms.

According to another particular aspect, the emulsion for topical use (E) as defined above is characterized in that the effective amount of said mixture ($M_1$) is such that the weight ratio between the glycerol and said mixture ($M_1$) is less than or equal to 10 and greater than or equal to 1, and more particularly less than or equal to 5 and greater than or equal to 2.

The emulsion for topical use (E) as defined above may comprise one or more adjuvants such as:
thickeners or gelling agents, for example linear or branched or crosslinked polymers of polyelectrolyte type, such as the partially or totally salified acrylic acid homopolymer, the partially or totally salified methacrylic acid homopolymer, the partially or totally salified 2-methyl-[(1-oxo-2-propenyl)amino]-1-propanesulfonic acid (AMPS) homopolymer, copolymers of acrylic acid and of AMPS, copolymers of acrylamide and of AMPS, copolymers of vinylpyrrolidone and of AMPS, copolymers of AMPS and of (2-hydroxyethyl) acrylate, copolymers of AMPS and of (2-hydroxyethyl) methacrylate, copolymers of AMPS and of hydroxyethylacrylamide, copolymers of AMPS and of N,N-dimethylacrylamide, copolymers of AMPS and of tris (hydroxymethyl)acrylamidomethane (THAM), copolymers of acrylic or methacrylic acid and of (2-hydroxyethyl) acrylate, copolymers of acrylic or methacrylic acid and of (2-hydroxyethyl) methacrylate, copolymers of acrylic or methacrylic acid and of hydroxyethylacrylamide, copolymers of acrylic or methacrylic acid and of THAM, copolymers of acrylic or methacrylic acid and of N,N-dimethylacrylamide, terpolymers of acrylic or methacrylic acid, of AMPS and of (2-hydroxyethyl) acrylate, terpolymers of acrylic or methacrylic acid, of AMPS and of (2-hydroxyethyl) methacrylate, terpolymers of acrylic or methacrylic acid, of AMPS and of THAM, terpolymers of acrylic or methacrylic acid, of AMPS and of N,N-dimethylacrylamide, terpolymers of acrylic or methacrylic acid, of AMPS and of acrylamide, copolymers of acrylic acid or methacrylic acid and of alkyl acrylates, the carbon chain of which comprises between 4 and 30 carbon atoms and more particularly between 10 and 30 carbon atoms, copolymers of AMPS and of alkyl acrylates, the carbon chain of which comprises between 4 and 30 carbon atoms and more particularly between 10 and 30 carbon atoms, linear, branched or crosslinked terpolymers of at least one monomer having a free, partially salified or totally salified strong acid function, with at least one neutral monomer, and at least one monomer of formula (VIII):

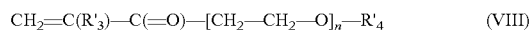

$$CH_2=C(R'_3)-C(=O)-[CH_2-CH_2-O]_n-R'_4 \qquad (VIII)$$

wherein R'3 represents a hydrogen atom or a methyl radical, R'4 represents a linear or branched alkyl radical comprising from eight to thirty carbon atoms and n represents a number greater than or equal to one and less than or equal to fifty; the linear or branched or crosslinked polymers of polyelectrolyte type that can be combined with the oil-in-water emulsion that is a subject of the present invention may be in the form of a solution, of an aqueous suspension, of a water-in-oil emulsion, of an oil-in-water emulsion, or of a powder, for example the products sold under the names Simulgel™ EG, Simulgel™EPG, Sepigel™ 305, Simulgel™ 600, Simulgel™ NS, Simulgel™ INS 100, Simulgel™ FL, Simulgel™ A, Simulgel™ SMS 88, Sepinov™EMT 10, Sepiplus™400, Sepiplus™265, Sepiplus™S, Sepimax™Zen, Aristoflex™AVC, Aristoflex™AVS, Novemer™EC-1, Novemer™EC 2, Aristoflex™HMB, Cosmedia™SP, Flocare™ET 25, Flocare™ET 75, Flocare™ET 26, Flocare™ET 30, Flocare™ET 58, Flocare™PSD 30, Viscolam™AT 64, Viscolam™AT 100; polysaccharides consisting only of monosaccharides, such as glucans or glucose homopolymers, glucomannoglucans, xyloglycans, galactomannans of which the degree of substitution (DS) of the D-galactose units on the main chain of D-mannose is between 0 and 1, and more particularly between 1 and 0.25, such as galactomannans originating from cassia gum (DS=⅕), from locust bean gum (DS=¼), from tara gum (DS=⅓), from guar gum (DS=½), from fenugreek gum (DS=1); polysaccharides consisting of monosaccharide derivatives, such as sulfated galactans and more particularly carrageenans and agar, uronans and more particularly algins, alginates and pectins, heteropolymers of monosaccharides and of uronic acids and more particularly xanthan gum, gellan gum, exudates of gum arabic and of karaya gum, glucosaminoglycans; cellulose, cellulose derivatives such as methylcellulose, ethylcellulose, hydroxypropylcellulose, silicates, starch, hydrophilic starch derivatives, polyurethanes;
    film-forming compounds;
    hydrotropic agents;
    plasticizers;
    opacifiers and/or nacreous agents, such as sodium or magnesium palmitate, stearate or hydroxystearate, ethylene or polyethylene glycol monostearates or distearate, fatty alcohols, styrene homopolymers and copolymers, such as the styrene acrylate copolymer sold under the name Montopol™ OP1 by SEPPIC.
    texturing agents, such as the lauroyl lysine sold under the name Aminohope™LL by Ajinomoto, the octenyl starch succinate sold under the name Dryflo™ by National Starch, the myristyl polyglucoside sold by SEPPIC under the name Montanov™ 14, cellulose fibers, cotton fibers, chitosan fibers, talc, sericite, mica;
    overfatting agents;
    sequestrants;
    chelating agents;
    nonionic surfactants such as ethoxylated derivatives of fatty alcohols comprising from 8 to 12 carbon atoms; ethoxylated derivatives of fatty acids comprising from 8 to 12 carbon atoms; ethoxylated derivatives of fatty esters comprising from 8 to 12 carbon atoms; ethoxylated derivatives of monoglycerides comprising from 8 to 12 carbon atoms; alkyl polyglycosides of formula (II):

$$R_2\text{—}O\text{—}(S)_y\text{—}H \quad\quad (II),$$

wherein y represents a decimal number between 1 and 5, S represents the residue of a reducing sugar and $R_2$ represents a linear or branched, saturated or unsaturated alkyl radical having from 5 to 16 carbon atoms, preferably from 8 to 14 carbon atoms, or a mixture of compounds of formula (II), for example caprylyl capryl glucosides, sold in particular under the brand name Oramix™CG 110, decylglucoside, sold in particular under the brand name Oramix™NS 10;
    antioxidants, such as EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S (INCI name: Tetrasodium Glutamate Diacetate);
    fragrances;
    preservatives;
    conditioning agents;
    active ingredients intended to provide a treating action with respect to the skin or the hair, such as vitamins and derivatives thereof, especially esters thereof, such as retinol (vitamin A) and the esters thereof (retinol palmitate, for example), ascorbic acid (vitamin C) and the esters thereof, sugar derivatives of ascorbic acid (such as ascorbyl glucoside), tocopherol (vitamin E) and the esters thereof (such as tocopheryl acetate), vitamin B3 or B10 (niacinamide and derivatives thereof); compounds showing a soothing action, especially Sepicalm™ S, allantoin and bisabolol; anti-inflammatories; compounds showing a moisturizing action, such as urea, hydroxyureas, glycerolglucoside, diglycerolglucoside, polyglycerylglucosides; polyphenol-rich plant extracts, such as grape extracts, pine extracts, wine extracts, olive extracts; compounds showing a slimming or lipolytic action, such as caffeine or derivatives thereof, Adiposlim™, Adipoless™, fucoxanthin; N-acylated proteins; N-acylated peptides, such as Matrixil™; N-acylated amino acids; partial hydrolyzates of N-acylated proteins; amino acids; peptides; total protein hydrolyzates; soybean extracts, for example Raffermine™; wheat extracts, for example Tensine™ or Gliadine™; plant extracts, such as tannin-rich plant extracts, isoflavone-rich plant extracts or terpene-rich plant extracts; extracts of freshwater or seawater algae; marine plant extracts; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5; Octopirox™ or Sensiva™ SC50; compounds showing an energizing or stimulating property, such as Physiogenyl™ panthenol and derivatives thereof, such as Sepicap™ MP; anti-aging active agents, such as Sepilift™ DPHP, Lipacide™ PVB, Sepivinol™, Sepivital™, Manoliva™, Phyto-Age™ Timecode™; Survicode™; anti-photoaging active agents; agents for protecting the integrity of the dermoepidermal junction; active agents for increasing the synthesis of extracellular matrix components such as collagen, elastins, glycosaminoglycans; active agents which act favorably on chemical cell communication, such as cytokines, or physical cell communication, such as integrins; active agents which create a "heating" sensation on the skin, such as skin microcirculation activators (such as nicotinic acid derivatives) or products which create a feeling of "freshness" on the skin (such as menthol and derivatives); active agents for improving skin microcirculation, for example veinotonics; draining active agents; active agents for decongestive purposes, such as extracts of *Ginkgo biloba*, of ivy, of horse chestnut, of bamboo, of ruscus, of butcher's broom, of *Centella asiatica*, of fucus, of rosemary, of willow; agents for tanning or browning the skin, for instance dihydroxyacetone (DHA), erythrulose, mesotartaric aldehyde, glutaraldehyde, glyceraldehyde, alloxan, ninhydrin, plant extracts, for instance extracts of redwood of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in European patent application EP 0 971 683; agents known for their action of facilitating and/or accelerating tanning and/or browning of the human skin and/or for their action of coloring the human skin, for example carotenoids (and more particularly beta-carotene and gamma-carotene), the product sold under the trade name "Carrot oil" (INCI name: *Daucus Carota, Helianthus annuus* Sunflower oil) by Provital, which contains carotenoids, vitamin E and vitamin K; tyrosine and/or the derivatives thereof, known for their effect on accelerating tanning of the human skin in combination with exposure to ultraviolet radiation, for instance the product sold under the trade name "SunTan Accelerator™" by Provital, which contains tyrosine and riboflavins (vitamin B), the tyrosine and tyrosinase complex sold under the trade name "Zymo Tan Complex" by Zymo Line, the product sold under the trade name MelanoBronze™ (INCI name: Acetyl Tyrosine, Monk's pepper extract (Vitex Agnus-castus)) by Mibelle, which contains acetyl tyrosine, the product sold under the trade name Unipertan VEG-24/242/2002 (INCI name: butylene glycol and Acetyl Tyrosine and hydrolyzed vegetable protein and Adenosine triphosphate) by Unipex, the product sold under the trade name "Try-Excell™" (INCI name: Oleoyl Tyrosine and Luffa Cylindrica (Seed) Oil and Oleic acid) by Sederma, which contains extracts of marrow seed (or loofah oil), the product sold under the trade name "Actibronze™" (INCI name: hydrolyzed wheat protein and acetyl tyrosine and copper gluconate) by Alban Muller, the product sold under the trade name Tyrostan™ (INCI name: potassium caproyl tyrosine) by Synerga, the product sold under the trade name Tyrosinol (INCI name: Sorbitan Isostearate, glyceryl oleate, caproyl Tyrosine) by Synerga, the product sold under the trade name InstaBronze™ (INCI name: Dihydroxyacetone and acetyl tyrosine and copper gluconate) sold by Alban Muller, the product sold under the trade name Tyrosilane (INCI name: methylsilanol and acetyl tyrosine) by Exymol; peptides known for their melanogenesis-activating effect, for example the product sold under the trade name Bronzing SF Peptide powder (INCI name: Dextran and Octapeptide-5) by Infinitec Activos, the product sold under the trade name Melitane (INCI name: Glycerin and Aqua and Dextran and Acetyl hexapeptide-1) comprising the acetyl hexapeptide-1 known for its alpha-MSH agonist action, the product sold under the trade name Melatimes Solutions™ (INCI name: Butylene glycol, Palmitoyl Tripeptide-40) by Lipotec, sugars and sugar derivatives, for instance the product sold under the trade name Tanositol™ (INCI name: inositol) by Provital, the product sold under the trade name Thalitan™ (or Phycosaccharide™ AG) by CODIF international (INCI name: Aqua and hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the trade name Melactiva™ (INCI name: Maltodextrin, *Mucuna Pruriens* Seed extract) by Alban Muller, flavonoid-rich compounds, for instance the product sold under the trade name "Biotanning" (INCI name: Hydrolyzed citrus Aurantium *dulcis* fruit extract) by Silab and known to be rich in lemon flavonoids (of hesperidin type);

mineral fillers or pigments, such as titanium dioxide, brown iron oxides, yellow iron oxides, black iron oxides, or red iron oxides or else white or colored nacreous pigments such as titanium mica;

particles which provide a visual effect or which are intended for the encapsulating of active agents;

exfoliating particles;

optical brighteners;

insect repellents.

The oil-in-water emulsion (E) as defined above can be packaged in a bottle, in a device of pump "bottle" type, in pressurized form in an aerosol device, in a device provided with a perforated wall such as a grille, or in a device provided with a roll-on applicator.

Another subject of the invention is the use of an oil-in-water type emulsion for topical use (E) as defined above as product for cleansing and/or caring for the human skin, and also a cosmetic method for cleansing and/or caring for the human skin, characterized in that an effective amount of the oil-in-water type emulsion for topical use (E) as defined above is applied to said human skin.

The following examples illustrate the invention without, however, limiting it.

DESCRIPTION OF THE PREFERRED EMBODIMENTS

Example 1: Preparation of Oil-In-Water Emulsions According to the Invention, Comprising a Mixture ($M_1$), and of Comparative Oil-In-Water Emulsions Three oil-in-water emulsions according to the invention, denoted ($E_1$), ($E_2$) and ($E_3$), the weight proportions of the constituents of which are indicated in table 1, and 8 comparative oil-in-water emulsions denoted ($F_1$) to ($F_8$), the weight proportions of the constituents of which are indicated in table 2 below, are prepared. The common preparation process for the oil-in-water emulsions according to the invention and for the comparative oil-in-water emulsions is as follows:

The tested mixture ($M_1$) is poured into a beaker at a temperature of 75° C., then the following are dispersed gradually and, depending on the case, successively: the caprylic/capric triglyceride, the Simulsol™165, the hexadecanol-1, the stearic acid, the Sepiplus™S (thickening polyelectrolyte), the Primol™352, the Sepicide™HB, with mechanical stirring at 80 revolutions/minute;

the aqueous phase comprising the water, the glycerol and the tetrasodium EDTA are poured into a beaker at a temperature of 75° C.;

the contents of the beaker comprising the fatty phase are gradually added to the aqueous phase at a temperature of 75° C. then placed under the action of a rotor-stator system for 4 minutes at a rate of 4000 revolutions per minute the mixture thus obtained is cooled with anchor type stirring for twenty minutes, then emptied out so as to obtain the oil-in-water emulsions ($E_1$) to ($E_3$) according to the invention and the comparative oil-in-water emulsions ($F_1$) to ($F_8$).

TABLE 1

|  | Emulsion | | |
| --- | --- | --- | --- |
|  | ($E_1$) | ($E_2$) | ($E_3$) |
| Fatty phase | | | |
| $C_8$-$C_{10}$ triglycerides | 3% | 3% | 4% |
| Sepiplus ™ S[(1)] | 1% | 1% | 1% |
| Simulsol ™165[(2)] | 2% | 2% | 2% |
| Hexadecanol-1 | 1.5% | 1.5% | 2.5% |
| Primal 352[(3)] | 4% | 4% | 5% |
| Stearic acid | 0.2% | 0.2% | 0.2% |

TABLE 1-continued

| | Emulsion | | |
|---|---|---|---|
| | (E₁) | (E₂) | (E₃) |
| Sepicide HB⁽⁴⁾ | 1% | 1% | 1% |
| Emosmart ™L19⁽⁵⁾ | 5% | 0% | 0% |
| Emogreen ™L15⁽⁶⁾ | 0% | 5% | 5% |
| Aqueous phase | | | |
| Water | Qs 100% | Qs 100% | Qs 100% |
| Glycerol | 10% | 10% | 10% |
| Tetrasodium EDTA | 0.2% | 0.2% | 0.2% |

TABLE 2

| | Emulsion | | |
|---|---|---|---|
| | (F₁) | (F₂) | (F₃) |
| Fatty phase | | | |
| C₈-C₁₀ triglycerides | 3% | 3% | 3% |
| Sepiplus ™ S⁽¹⁾ | 1% | 1% | 1% |
| Simulsol ™165⁽²⁾ | 2% | 2% | 2% |
| Hexadecanol-1 | 1.5% | 1.5% | 1.5% |
| Primal 352⁽³⁾ | 4% | 4% | 4% |
| Stearic acid | 0.2% | 0.2% | 0.2% |
| Sepicide HB⁽⁴⁾ | 1% | 1% | 1% |
| Emosmart ™L15⁽⁷⁾ | 5% | 0% | 0% |
| Emosmart ™V21⁽⁸⁾ | 0% | 5% | 0% |
| Isohexadecane | 0% | 0% | 5% |
| Aqueous phase | | | |
| Water | Qs 100% | Qs 100% | Qs 100% |
| Glycerol | 10% | 10% | 10% |
| Tetrasodium EDTA | 0.2% | 0.2% | 0.2% |

| | Emulsion | | | | |
|---|---|---|---|---|---|
| | (F₄) | (F₅) | (F₆) | (F₇) | (F₈) |
| Fatty phase | | | | | |
| C₈-C₁₀ triglycerides | 3% | 3% | 3% | 4% | 4% |
| Sepiplus ™ S⁽¹⁾ | 1% | 1% | 1% | 1% | 1% |
| Simulsol ™165⁽²⁾ | 2% | 2% | 2% | 2% | 2% |
| Hexadecanol-1 | 1.5% | 1.5% | 1.5% | 2.5% | 2.5% |
| Primal 352⁽³⁾ | 4% | 4% | 4% | 5% | 5% |
| Stearic acid | 0.2% | 0.2% | 0.2% | 0.2% | 0.2% |
| Sepicide HB⁽⁴⁾ | 1% | 1% | 1% | 1% | 1% |
| Isododecane | 5% | | | | |
| Lanol ™ 99⁽⁹⁾ | | 5% | | | |
| DC 345⁽¹⁰⁾ | | | 5% | 5% | 5% |
| Aqueous phase | | | | | |
| Water | Qs 100% | Qs 100% | | Qs 100% | Qs 100% |
| Glycerol | 10% | 10% | 10% | 10% | 20% |
| Tetrasodium EDTA | 0.2% | 0.2% | 0.2% | 0.2% | 0.2% |

⁽¹⁾(Sepiplus ™S): Thickening agent (INCI name: hydroxy ethyl acrylate/sodium acryloyldimethyl taurate copolymer & Polyisobutene & PEG-7 trimethylolpropane coconut oil);
⁽²⁾(Simulsol ™165): Emulsifier (INCI name: PEG-100 stearate & Glyceryl stearate);
⁽³⁾(Primol ™352): Emollient (INCI name: Paraffin Oil);
⁽⁴⁾(Sepicide ™HB): Preservative (INCI name: phenoxyethanol/methylparaben/ethylparaben/propylparaben/isobutylparaben);
⁽⁵⁾(Emosmart ™L19): Mixture of saturated cyclic or acyclic, linear or branched hydrocarbons comprising, for 100% of its weight: i) 13.20% by weight of linear alkanes comprising from 15 to 19 carbon atoms, ii) 55.00% by weight of isoalkanes comprising from 15 to 19 carbon atoms, iii) 31.80% of cycloalkanes comprising from 15 to 19 carbon atoms;
⁽⁶⁾(Emogreen ™L15): Mixture comprising, for 100% of its weight: i) 3.7% of linear alkanes comprising from 15 to 19 carbon atoms, ii) 96% of isoalkanes comprising from 15 to 19 carbon atoms, iii) 0.3% of cycloalkanes comprising from 15 to 19 carbon atoms;
⁽⁷⁾(Emosmart ™L15): Mixture comprising, for 100% of its weight: i) 9.26% by weight of linear alkanes comprising from 13 to 15 carbon atoms, ii) 39.06% of isoalkanes comprising from 13 to 15 carbon atoms, iii) 51.68% of cycloalkanes comprising from 13 to 15 carbon atoms;
⁽⁸⁾(Emosmart ™V21): Mixture comprising, for 100% of its weight: i) 15.99% by weight of linear alkanes comprising from 18 to 21 carbon atoms, ii) 59.90% by weight of isoalkanes comprising from 18 to 21 carbon atoms, iii) 24.11% of cycloalkanes comprising from 18 to 21 carbon atoms;
⁽⁹⁾(Lanol ™ 99): Emollient (INCI name: isononyl isononate);
⁽¹⁰⁾(DC 345): (INCI name: cyclopentasiloxane & cyclohexasiloxane).

Evaluation of the Tacky Properties of the Oil-In-Water Emulsions According to the Invention, Comprising a Mixture ($M_1$), and of Comparative Oil-In-Water Emulsions.

Principle of the Measurement

The characterization of each emulsion tested by a mean value of 3 measured values of the adhesion strength to which the Peltier plate is subjected during compressions and rises.

Material and Equipment

The measurements are performed by means of a DHR2 model rheometer (of the TA Instrument brand) equipped with a support of Peltier plate type on which a plexiglass surface is placed, on which the emulsion to be tested is deposited.

Procedure

An amount of 63 microliters of the emulsion to be characterized is deposited on a plexiglass sheet arranged on a Peltier plate, the temperature of which is set to 40° C. After deposition of the sample, it is spread for 10 seconds by a rotational stress of the upper mobile plate on each emulsion. The normal strength which holds the upper mobile plate on the Peltier plate (or the adhesion strength) is measured during a succession of 48 movements of compression followed by rises.

Expression of the Results

For each emulsion tested, the values obtained between 4000 and 6000 s of the compression/tension cycle are considered. The mean and the standard deviations are calculated. The test is repeated at least 3 times and the mean overall value of the adhesion strength or tension is then determined.

Results

The results obtained are recorded in table 3 hereinafter.

TABLE 3

| Emulsion tested | (E₁) | (E₂) | (E₃) | (F₁) | (F₂) |
|---|---|---|---|---|---|
| Mean of the adhesion strength (in Newtons) | 2.28 | 5.06 | 4.78 | 11.9 | 6.23 |

| Emulsion tested | (F₃) | (F₄) | (F₅) | (F₆) | (F₇) | (F₈) |
|---|---|---|---|---|---|---|
| Mean of the adhesion strength (in Newtons) | 8.21 | 11.42 | 3.76 | 7.67 | 7.83 | 11.57 |

Analysis of the Results

The results given in table 3 clearly demonstrate that the mean strengths measured for the emulsions ($E_1$), ($E_2$) and ($E_3$) are lower than the means recorded for the comparative emulsions ($F_1$) to ($F_8$), and more particularly lower than the values of 7.67, 7.83 and 11.57 associated with the reference emulsions ($F_6$), ($F_7$) and ($F_8$), respectively, comprising the reference agent DC345.

The invention claimed is:

1. A method for reducing a tacky effect of an oil-in-water emulsion for topical use ($E_0$) comprising, for 100% of said $E_0$ a weight:
   from 10% to 25% by weight of glycerol,
   from 90% to 70% by weight, of a cosmetically acceptable aqueous phase ($A_0$);
   from 10% to 30% by weight of a fatty phase ($G_0$), said fatty phase ($G_0$) comprising, for 100% of said $G_0$ a weight, from 2% to 8% by weight of at least one oil-in-water surfactant and from 88% to 99% by weight, of at least one oil and/or one wax, wherein said emulsion ($E_0$) does not comprise any synthetic polymers comprising silicone or any third compound of silicone nature, wherein an effective amount of a mixture ($M_1$) of cyclic or acyclic, linear or branched saturated hydrocarbons, among which at least 95% by weight comprise from fifteen to nineteen carbon atoms, is incorporated into said oil-in-water type emulsion for topical use ($E_0$), wherein said effective amount of a mixture (M1) is from 5% to 20% by weight of said oil-in-water emulsion, and the weight ratio between the glycerol and said mixture ($M_1$) is less than or equal to 5 and greater than or equal to 2, and wherein said mixture ($M_1$) comprises, for 100% of its weight either:

branched alkanes of greater than or equal to 80% by weight and less than or equal to 100% by weight, linear alkanes of greater than or equal to 0% by weight and less than or equal to 15% by weight, and cycloalkanes of greater than or equal to 0% by weight and less than or equal to 5%, by weight and up to 5% by weight of said cyclic, acyclic, linear or branched hydrocarbons comprise less than fifteen carbon atoms or more than nineteen carbon atoms; or branched alkanes of greater than or equal to 40% by weight and less than or equal to 100% by weight, linear alkanes of greater than or equal to 0% by weight and less than or equal to 20% by weight and cycloalkanes of greater than or equal to 0% by weight and less than or equal to 40% by weight, and 100% by weight of said cyclic or acyclic, linear or branched hydrocarbons comprise from fifteen to nineteen carbon atoms.

2. The method according to claim 1, wherein said mixture ($M_1$) comprises, for 100% of said $M_1$ a weight either:

branched alkanes of greater than or equal to 90% and less than or equal to 100% by weight linear alkanes of greater than or equal to 0% by weight and less than or equal to 10% by weight and cycloalkanes of greater than or equal to 0% by weight and less than or equal to 1% by weight, and up to 5% by weight of said cyclic, acyclic, linear or branched hydrocarbons comprise less than fifteen carbon atoms or more than nineteen carbon atoms; or branched alkanes of greater than or equal to 50% by weight and less than or equal to 100% by weight linear alkanes of greater than or equal to 0% by weight and less than or equal to 15% by weight, and cycloalkanes of greater than or equal to 0% by weight and less than or equal to 35% by weight, and 100% by weight of said cyclic or acyclic, linear or branched hydrocarbons comprise from fifteen to nineteen carbon atoms.

3. The method according to claim 2, wherein said mixture (M1) comprises for 100% of said $M_1$ a weight:
i) 3.7% of linear alkanes comprising from fifteen to nineteen carbon atoms,
ii) 96% of isoalkanes comprising from fifteen to nineteen carbon atoms, and
iii) 0.3% of cycloalkanes comprising from fifteen to nineteen carbon atoms.

4. The method according to claim 2, wherein said mixture (M1) comprises for 100% of said $M_1$ a weight:
i) 13.20% of linear alkanes comprising from fifteen to nineteen carbon atoms,
ii) 55.00% of isoalkanes comprising from fifteen to nineteen carbon atoms, and
iii) 31.80% of cycloalkanes comprising from fifteen to nineteen carbon atoms.

* * * * *